United States Patent [19]

Hackman et al.

[11] Patent Number: 4,480,138

[45] Date of Patent: Oct. 30, 1984

[54] HYDROFORMYLATION PROCESS

[75] Inventors: E. B. Hackman, Corpus Christi; L. D. Zeagler, Pampa, both of Tex.

[73] Assignee: Celanese Corporation, New York, N.Y.

[21] Appl. No.: 433,749

[22] Filed: Oct. 12, 1982

[51] Int. Cl.$^3$ .............................................. C07C 45/50
[52] U.S. Cl. .................................................. 568/454
[58] Field of Search ......................... 568/454, 909, 492

[56] References Cited

U.S. PATENT DOCUMENTS

| | | | |
|---|---|---|---|
| 3,527,809 | 9/1970 | Pruett et al. | 568/454 |
| 3,965,192 | 6/1976 | Booth | 568/454 |
| 4,148,830 | 4/1979 | Pruett et al. | 568/454 |
| 4,151,209 | 4/1979 | Paul et al. | 568/454 |
| 4,159,999 | 7/1979 | Stautzenberger | 568/454 |
| 4,287,369 | 9/1981 | Harris et al. | 568/454 |
| 4,329,511 | 5/1982 | Hackman et al. | 568/454 |

Primary Examiner—Werren B. Lone
Attorney, Agent, or Firm—L. I. Grim; M. Turken

[57] ABSTRACT

In hydroformylating an olefinic compound to produce an aldehyde derivative thereof employing as a catalyst a complex of a Group VIII metal and an organic ligand dissolved in an inert liquid reaction solvent, improvements in production efficiencies and product separation from reaction product in solution are achieved in using as the inert liquid reaction medium, a saturated alpha-olefin oligomer free of naphthenic and aromatic hydrocarbons having the appropriate viscosity, average molecular weights and flash point properties which are required in the hydroformylating reaction.

7 Claims, No Drawings

HYDROFORMYLATION PROCESS

BACKGROUND OF THE INVENTION

Processes for hydroformylating an olefin to prepare a carbonyl derivative containing one carbon atom more than the parent olefin by reacting the olefin with synthesis gas in the presence of a Group VIII metal, e.g. rhodium, in complex combination with an organic ligand, carbon monoxide also being a component of the catalyst complex, are well known in the art and of growing industrial importance. This technology is summarized, for example, in U.S. Pat. No. 3,527,809 to Pruett et al. The olefin reactant is contacted with the catalyst and the synthesis gas (a mixture of carbon monoxide and hydrogen) in the presence of a liquid reaction medium, which may or may not comprise a separate inert liquid solvent species. A gas comprising the carbon monoxide and hydrogen is typically bubbled through the liquid reaction medium which is contained in a hydroformylation reactor which can be mechanically stirred or which may be agitated solely by the action of reactant gas being bubbled therethrough. The gas, in addition to hydrogen and carbon monoxide, may also contain vapors of the reactant olefin, in a proportion which will depend upon such factors as reaction conversion rate and the volatility of the olefin.

The aldehyde hydroformylation product can be recovered from the liquid hydroformylation reaction medium in various ways, but, especially when the aldehyde is of comparatively low molecular weight, e.g., when it contains from three to about seven carbon atoms and especially when it contains from three to about five carbon atoms, it is conveniently stripped out in vapor form by distillation, evaporation, or, especially, by being stripped out of the hydroformylation reaction zone in the gases which are being bubbled through the liquid contained therein. Hershman et al have described this technology in "I&EC Product Research and Development" 8, pp 372-375 (1969) in a discussion of the hydroformylation of propylene in a gas-sparged reactor.

In more recent years various patents and other publications have appeared directed to the use of special reaction solvents and/or special techniques for stripping the aldehyde product out of the liquid reaction medium. For example, U.S. Pat. No. 4,148,830 (Pruett et al) recommends using high-boiling reaction by-products as the reaction solvent, with the aldehyde product being subsequently recovered from the reaction medium in a separate vaporization operation.

In a related hydroformylation process, U.S. Pat. No. 4,329,511 issued to Hackman et al describes the use of a high molecular weight, high-boiling inert liquid reaction solvent in proportions of about 40 to about 95% by weight of the liquid reaction product, for purposes of controlling the rate of stripping at a level such that at a given molar concentration (relatively low) of product aldehyde in the mixture, and the mole fraction of the aldehyde in the mixture will be relatively high. The solvents disclosed as suitable are those having a molecular weight of at least about 700 and are capable of dissolving the catalyst and olefin. The specific solvents used are not considered critical as long as they are: (1) miscible with the catalyst system; (2) miscible with the reactants; (3) miscible with the reaction products; (4) low in volatility so as to facilitate stripping reaction product and by-products from it and (5) chemically inert in the hydroformylation reaction system. The disclosed solvents include, for example, alkyl-substituted benzene; pyridine and alkyl-substituted pyridines; tertiary amines; high boiling esters such as dialkyldicarboxylates and triorganophosphates as well as esters of polyols such as trimethylolpropane and pentaerythritol; ketones; alcohols such as butanols; nitriles such as acetonitriles; and hydrocarbons such as kerosene, mineral oil, cyclohexane, naphtha, etc. and aromatics such as biphenyl. In addition to these solvents, the use of polyalkylene glycols such as polyethylene glycol and polypropylene glycol having molecular weights greater than about 700 are stated to be particularly desirable because of their availability and their desirable properties for use as a hydroformylation solvent.

A further related hydroformylation process is described in U.S. Pat. No. 4,151,209 to Paul et al, which describes techniques for recovering aldehyde products from the reaction products by distillation, stripping, employing the ratio of phosphorus contained in the high-boiling reaction by-products to the phosphorus contained in the ligand (triorganophosphine ligand) which is present, as the primary control. Although the claimed improvement of the Paul et al process is different from that of the process of U.S. Pat. No. 4,329,511, similar solvents have been found to be satisfactory for use in the hydroformylation reactions described in both of these patents.

As has been described above, there are many satisfactory solvents which can be used in the hydroformylation of olefins to aldehydes. It is the objective of this invention to provide a hydroformylation process using a new solvet which has all the necessary properties required of a hydroformylation solvent but also provides improvements in the efficiency of the production and recovery of aldehydes from the hydroformylation reaction products.

SUMMARY OF THE INVENTION

For a hydroformylation process of an alpha-ethylenically unsaturated compound with a Group VIII metal catalyst in complex combination with an organic ligand dissolved in a solvent, it has been discovered that the use as the solvent of a saturated alpha-olefin oligomer free of naphthenic and aromatic hydrocarbons comprising a major proportion of molecules containing from 30 to 50 carbon atoms, and having an average molecular weight, specific viscosity and flash point, within certain specified ranges provides improvements in product efficiencies and product separation from the remaining reaction products. The alpha-olefin oligomer used in this invention has all the necessary properties necessary for a solvent to be used in a hydroformylation reaction. These properties include the miscibility with the catalyst system, the reactants and reaction products; low volatility so as to facilitate stripping the reaction product and by-products from it; thermal and chemical stability to prevent detrimental effects such as foaming; and no significant levels of contaminants which would poison the catalyst. Of specific interest, it has been discovered that the rousing factor of the hydroformylation reactants in the presence of the decene oligomer solvent used in this invention is lower on a comparative basis than the rousing factor of the reactants in the presence of an equivalent (in viscosity) mineral oil solvent. The "rousing factor" is defined as the ratio of aerated volume to unaerated volume. As the rousing factor decreases, a higher volume of liquid reactants in the reactor is available. This means that reactants with a lower rousing factor will provide an increase in the capacity of the reactor compared to the reactants with higher rousing factors. Thus, the use of an alpha-olefin as the solvent provides improvements in its use in the hydroformylation process compared to an equivalent mineral oil as well as providing an excellent recovery of the aldehyde product from the reaction product solution and at the same time reduces the formation of undesired condensation products formed from the aldehyde in the reaction medium.

DETAILED DESCRIPTION AND PREFERRED EMBODIMENTS

The present process improvement is directed to liquid phase catalytic hydroformylations of alpha olefins in the presence of saturated alpha-olefin oligomers free of naphthenic and aromatic hydrocarbons composed of molecules containing 30 to 50 carbon atoms and having a molecular weight and physical properties within certain specified ranges. The hydroformylation technology which is used in this invention is generally well known.

For this invention, Group VIII metals broadly, particularly rhodium and ruthenium and especially rhodium, are employed in organometallic complexes as catalysts for the reaction of a synthesis gas (i.e., a mixture of hydrogen and carbon monoxide) with alpha-olefins to form aldehyde derivatives of the olefins which have one more carbon atom that the parent olefin. A wide range of olefinic feedstocks can be employed in such processes, including substituted olefins and especially olefins having no heteroatoms other than oxygen. While the present process improvement is broadly applicable to the hydroformylation of olefins of 2 to 20 carbon atoms, its most useful applications are with olefins, and especially alpha-olefins of 2 to 8 carbon atoms. The process is particularly suitable for hydroformylating ethylene and propylene to propionaldehyde and n-butyraldehyde respectively.

These known hydroformylation processes are carried out at superatmospheric pressure, typically under a partial pressure of about 4 to 20 atmospheres of hydrogen and carbon monoxide combined and with the molar ratio of hydrogen to carbon monoxide being about 0.5:1 to 10:1. The hydroformylation reaction temperature is normally within the range of 80° C. to 150° C., preferably in the range from about 100° C. to about 120° C.

The liquid reaction medium or catalyst solution which is employed comprises, (a) the catalyst complex, (b) typically, an excess of the organic ligand employed in forming the complex over and above the amount required to complex the metallic component of the catalyst, (c) the hydroformylation reaction product along with by-products typically resulting from undesired condensation of the hydroformylation product aldehyde with itself, (d) a quantity of the olefin being hydroformylated, in an amount varying with the molecular weight of said olefin (the proportion of liquid olefin in the reaction medium usually being greater with high molecular weight olefins than with lower alkenes such as ethylene), and (e) involving the processing of olefins of low to moderate molecular weight, an inert reaction solvent comprising alpha-olefin oligomer used herein.

The catalyst contained in the reaction mixture can be, as known in the art, any Group VIII metal complexed with an organic ligand. The catalytic metal is complexed with hydrogen and carbon monoxide as well as with an organic ligand. While many organic ligands can be employed, those of particular significance comprise either monodentate or polydentate triorganophosphines, triorganophosphites, triorganoarsines, or triorganostibines, with the phosphines and phosphites being of particular industrial importance. Simple monodentate phosphines and phosphites, as exemplified by triphenylphosphine and triphenylphosphite, are commonly employed industrially. However, polydentate ligands have advantages in that the large excesses of ligand which are often used with the monodentate ligands are not needed. For example, the phosphine-modified ferrocene-based ligands as taught in U.S. Pat. No. 4,138,420 to Unruh et al, are applicable as well as the sterically restricted bidentate phosphorus-containing ligands described in U.S. Pat. No. 4,139,565. Ligands modified by the incorporation of electronegative substituents into the molecule also have advantages, as set forth in U.S. Pat. No. 4,152,344 to Unruh. The catalytic complex can be formed in situ in the hydroformylation reactor, or it can be preformed.

The concentration of catalyst to be maintained in the hydroformylation reaction medium is not critical to the successful employment of the present invention. Typically, however, when the catalytic metal is rhodium and when the ligand is triphenylphosphine, the liquid reaction medium will contain about 0.01 to 1.0% rhodium and up to about 20% or more triphenylphosphine by weight where suppression of iso-aldehydes is desired. In hydroformylating ethylene, the iso-aldehyde problem does not exist, and very low ligand concentrations can be employed, e.g. 1% or less. In the absence of the added inert reaction solvent with which the present invention is concerned, the triphenylphosphine content in hydroformylating propylene, for example, may be as high as about 40%. Typically, the ligand concentration will not exceed about 45 weight percent.

The solvent used in this invention is a saturated alpha-olefin oligomer free of naphthenic and aromatic hydrocarbons composed of molecules containing from 30 to 50 carbon atoms. The kinematic viscosity of the alpha-olefin oligomer at 100° C. is from about 3.0 centistokes to about 8.0 centistokes, preferably from about 3.5 to about 6.5, the average molecular weight is from about 450 to about 700, preferably from about 500 to about 570 and the flash point ranges from about 400° F. to about 570° F., preferably about 450° F. to about 500° F. The preferred alpha-olefin oligomer is a hydrogenated decene-1 (C-10 normal alpha-olefin) oligomer having the above described properties.

The present improved process is conducted in a manner similar to prior art hydroformylation process employing an added inert solvent. Mechanical agitation of the liquid contents of the hydroformylation reactor can be employed if desired, but it is simple and satisfactory to obtain adequate agitation by sparging the synthesis gas through the liquid reaction medium. A mixture of gases and vapors withdrawn from the top of the reaction vessel contains the aldehyde product in vapor form, as well as unreacted olefin. The aldehyde is recovered from these withdrawn gases and vapors, which are then recycled to the reaction sparger along with fresh olefin and synthesis gas. The reaction temperature and pressure are set at known prior art levels at which the hydroformylation reaction takes place at commercially satisfactory rates and yields. The rate of gas recycle can be varied to control the rate at which product is stripped out of the liquid reaction mixture contained in the reaction vessel.

An alternative mode of operation which can be employed in place of the above-described method for stripping product out of the reactor with the recycling gases is to withdraw a slip stream of liquid from the hydroformylation reactor and distill it to recover a distillate comprising the aldehyde product while leaving a distillation residue comprising the reaction solvent and catalyst, this residue then being returned to the hydroformylation reactor. Yet another alternative is to subject the withdrawn slip stream to simple evaporation, although distillation is preferable because it facilitates making a sharper separation between reaction products and high-boiling solvent.

For this invention, it is recommended that sufficient alpha-olefin oligmer be incorporated into the hydroformylation reaction medium such that the resulting liquid mixture contains at least about 50% of the alpha-olefin oligomer, computed on a product aldehyde-free basis. Lesser proportions of the diluent will have some effect, of course, but a proportion of at least 50% by weight is desirable. Proportions higher than about 50 weight percent are desirable, up to an upper limit which will be imposed by the fact that in many reaction systems there will be a substantial excess of ligand, e.g. triphenylphosphine, which will itself constitute a substantial fraction of the reaction medium. For example, the liquid may frequently contain about 30–40 weight percent of excess ligand which is thus unavoidably a substantial component. Broadly speaking, then, it is recommended that the diluent be incorporated into the reaction medium in a proportion of at least about 50% by weight, with lower proportions of the order of about 40% by weight or even less still being advantageous, while the upper limit is normally imposed by the fact that there are present other essential components such as the organic ligand which can be reduced in concentration only at the cost of reduced reactor throughput. In most situations the diluted reaction medium will contain, by weight, about 40% to about 85%, or more broadly about 40% to 95% of the high molecular weight diluent on the product aldehyde-free basis. Product aldehyde itself will typically amount to roughly 3% to 12% of the total reaction mixture.

The following examples are given to illustrate further the application of the invention. It will be understood that many variations can be made therefrom within the scope of the invention.

EXAMPLE 1

Ethylene was hydroformylated to produce propionaldehyde by being sparged, in admixture with synthesis gas and reaction recycle gas, through a catalyst containing liquid reaction medium in a hydroformylation reactor operated at 115° C. and 35 atmospheres absolute. The catalyst in this invention was added to the reaction mixture in the form of rhodium nitrate which reacts with the triphenylphosphine and gases to form an active rhodium complex. The reactor liquid is cooled by recirculating it through an external heat exchanger and back into the top of the top of the reaction vessel. The contents of the reactor were agitated by the action of the gas sparger. The gas sparged into the base of the reactor comprised, in mol percent, 55.3% hydrogen, 29.8% carbon monoxide, 10.1% ethylene, 1.6% nitrogen, 1.0% ethane, 1.5% propionaldehyde, and the remainder minor contaminants. This gas was fed at the rate of 553.6 gram mols per hour per liter of catalyst solution in the reactor itself, and the propionaldehyde stripped out of the catalyst solution with the exiting gases amounts to 22.3 gram mols per liter of catalyst solution per hour.

The reactor liquid through which the ethylene was sparged has the composition shown in Table I.

TABLE I

PROPIONALDEHYDE PRODUCTION LIQUID REACTION MEDIUM

| Component | Mol % | Wt % | gm Mols per Liter of Solution |
|---|---|---|---|
| Propionaldehyde | 36.8 | 6.3 | 1.073 |
| Total Heavy Ends (Average Molecular Weight = 200) | <2.0 | <1.2 | <0.058 |
| Triphenylphosphine | 7.2 | 5.6 | 0.021 |
| Triphenylphosphine Oxide | 0.7 | 0.6 | 0.020 |
| Rhodium | 0.2 | 0.5 | 0.006 |
| Alpha-Olefin Oligomer[1] | >53.1 | >86.25 | >1.549 |

[1]Decene oligomer having a viscosity at 99° C. of 6.02 centistokes, flash point 456° F. and an average molecular weight of 550. Carbon number distribution $C_{30}$ = 31 weight percent, $C_{40}$ = 46 weight percent and $C_{50}$ = 23 weight percent. Sold under the trademark Synfluid ® base Fluids as Gulf 6 cSt polyalphaolefin by Gulf Oil Chemical Company.

The reactor effluent gases were drawn out from the top of the reactor and were cooled to 40° C. at 34.67 atmospheres absolute pressure. The resulting condensate was drawn off as crude aldehyde production, and the uncondensed gas was recycled to the hydroformylation reactor. The effluent gases comprised, in mol percent, 56.3% hydrogen, 25.9% carbon monoxide, 11.4% propionaldehyde, 1.9% nitrogen, 2.4% ethylene, 1.2% ethane, with the remainder other minor contaminants.

With the reaction system operating in this manner, the space-time yield of propionaldehyde amounts to approximately 22.3 gm mols per hour per liter of catalyst solution. The molar density of the catalyst solution including the alpha-olefin oligomer was 2.9 gram mols per liter. The concentration of reaction heavy ends does not build up appreciably over an extended period of time, and the activity of the catalyst was also stable for extended periods.

While the process as exemplified here operates at 35 atmospheres pressure, lower pressures can be employed down to about 15 atmospheres, below which the reaction rate begins to fall off more than is normally desired. The only upper limit on pressure is imposed by economic considerations of apparatus design strength, although it will also be understood that, as pressure increases, the moles of stripping gas required per unit of aldehyde to be stripped out will increase for reasons obvious to those skilled in chemical engineering. Normally pressures will not exceed 70 atmospheres.

EXAMPLE 2

A comparison was made of the solubilities in decene oligomer solvent and a comparable mineral oil of rhodium present in the catalyst solutions obtained by stripping the reaction liquid resulting from the hydroformylation of ethylene to propionaldehyde and propylene to butyraldehyde. The initial solutions contained in addition to rhodium complex catalyst, a small amount of aldehyde product, triphenylphosphine, triphenylphosphine oxide, and in situ produced heavy ends solvent (high boiling reaction by-products resulting from the condensation of aldehyde product during the hydroformylation reaction).

The physical properties of the decene oligomer solvent and mineral oil used in the comparison are shown in Table II.

TABLE II

| Physical Constants | Decene Oligomer Solvent | Mineral Oil |
|---|---|---|
| Viscosity (centistokes) | | |
| 210° F. (99° C.) | 6.02 | 5.35 |
| 100° F. (38° C.) | 33.66 | 24.07 |
| Flash Point °F. | 456 | 385 |
| Specific Gravity | 0.827 | 0.860 |
| Average Molecular Weight | 550 | 370 |

The solutions were prepared by mixing 50 milliliters of catalyst solution obtained from the stripping of reactor liquid produced during the hydroformylation of ethylene to propionaldehyde in one instance with an equal volume (50 milliliters) of the decene oligomer solvent and in another instance an equal volume (50 milliliters) of the mineral oil at 110° C. and 100 pounds per square inch gauge nitrogen. The mixtures were allowed to cool and the decene oligomer or mineral oil phase separated from the heavy ends phase. Analysis of the original catalyst heavy ends solution, the recovered mineral oil layer and the recovered decene oligomer layer are listed in Table III as follows:

TABLE III

| | Rhodium, Parts Per Million | Wt. % of Original Rhodium in Layer | Triphenyl-phosphine (TTP) Wt. % | Wt. % of Original TPP in Layer | Triphenyl-phosphine Oxide (TPPO) Wt. % | Wt. % of Original TPPO in Layer |
|---|---|---|---|---|---|---|
| Original Catalyst Solution (Specific Gravity 1.0) | 1160 | — | 12.1 | — | 7.6 | — |
| Mineral Oil | <116 | 8.6 | 1.6 | 11.3 | 3.2 | 36 |
| Decene Oligomer Solvent | <118 | 8.4 | 2.5 | 17 | 2.9 | 31.5 |

The results indicate that similar amounts of catalytic rhodium present in a stripped ethylene hydroformylation liquid will be extracted by decene oligomer and mineral oil solvents. A slightly higher amount of the hydroformylation active ingredient triphenylphosphine present in the initial catalyst solution is extracted into the decene oligomer solvent than is extracted in the mineral oil layer. On the other hand, a slightly lower amount of undesirable triphenylphosphine oxide is extracted into the decene layer compared to the mineral oil layer. Triphenylphosphine oxide is not an active ingredient in the hydroformylation reaction and it is desirable to keep the amount of triphenylphosphine oxide to a minimum in the hydroformylation reaction.

The foregoing results are significant as an indication of the amounts of the various components which will be present in the reactor liquid after it is stripped of feeder gases and product, treated to regenerate the catalyst and used in the start-up of the reaction.

EXAMPLE 3

Using the same procedure as in Example 2, 200 milliliters of catalyst solution obtained by stripping the reaction liquid obtained in the hydroformylation of propylene to butyraldehyde was mixed with an equal volume (200 milliliters) of decene oligomer solvent in one instance and an equal volume (200 milliliters) of mineral oil in another instance at 116° C. under 100 pounds per square inch gauge nitrogen. The same decene oligomer solvent and mineral oil used in Example 2 were used in this comparison. The mixtures were allowed to cool and phase for 24 hours before the samples were taken for analysis. The analysis of the original catalyst heavy ends solution, the recovered mineral oil layer and the recovered decene oligomer solvent layer are indicated in Table IV as follows:

TABLE IV

| | Rhodium, Parts Per Million | Wt. % of Original Rhodium in Layer | Triphenyl-phosphine (TTP) Wt. % | Wt. % of Original TPP in Layer | Triphenyl-phosphine Oxide (TPPO) Wt. % | Wt. % of Original TPPO in Layer |
|---|---|---|---|---|---|---|
| Original Catalyst Solution (Specific Gravity 1.0) | 2914 | — | 28.1 | — | 6.3 | — |
| Mineral Oil | 402 | 11.9 | 12.4 | 37.9 | 1.4 | 19.1 |
| Decene Oligomer Solvent | 215 | 6.1 | 10.9 | 32.0 | 1.2 | 15.7 |

The results indicate that approximately one-half of the rhodium was extracted in the decene oligomer solvent compared to the amount of rhodium extracted in the mineral oil layer. The amount of triphenylphosphine and triphenylphosphine oxide extracted into the decene oligomer solvent is slightly lower than the amount extracted into the mineral oil.

The types of alpha-olefins which can be used in the formation of the oligomer solvents of this invention are those containing from 2 to 20 carbon atoms, preferably 6 to 18 carbon atoms, and most preferably decene. The oligomers produced are normally paraffins (alkanes) and for purposes of this invention the molecules of the solvent contain from 30 to 50 carbon atoms. The oligomers are hydrogenated at least once and if necessary a second dehydrogenation can be conducted to assure a saturated solvent. A distillation can isolate the different solvents having the desired properties such as viscosity, average molecular weight and flash points. As described in this specification, the liquid alpha-olefinic oligomers made in the above manner provide fluids with predetermined chemical and physical properties.

Mineral oil is obtained from the heavy distillates fraction of crude petroleum. The chemical compositions can vary depending on the source of the crude petroleum. The mineral oil can be recovered from crude petroleum by distillation on the basis of viscosity ranges which, in most instances, is the main parameter for the use of mineral oils.

EXAMPLE 4

For purposes of comparison, a determination of the solvent properties of various hydrocarbon solvents with respect to propionaldehyde and butyraldehyde was conducted in a high pressure vapor-liquid equilibrium (VLE) cell. The high pressure cell is a modified Othmer VLE cell which employs continuous condensation and recirculation of the vapor phase. Heat is input to a liquid contained in the main chamber. This heat vaporizes a portion of the liquid phase and creates a vapor phase which is in equilibrium with the liquid. The vapor phase is then condensed, collected in a condensate pot and returned to the main chamber. The solvents tested were various decene oligomer solvents and mineral oils, with physical properties as shown in Table V.

TABLE VII

| Solvent | Butyraldehyde* Vapor Pressure | | Butyraldehyde Vapor Pressure (psia) |
|---|---|---|---|
| | Butyraldehyde Concentration | | |
| | (Wt. %) | (Vol. %) | |
| 6cSt Decene Oligomer | 28.1 | 28.5 | 34.5 |
| " | 26.3 | 26.7 | 34.5 |
| " | 30.0 | 30.4 | 40.5 |
| " | 34.5 | 35.0 | 40.5 |
| Sunpar 150 Mineral Oil | 26.4 | 27.9 | 37.5 |
| " | 21.1 | 22.4 | 37.5 |
| " | 32.0 | 33.7 | 41.0 |
| " | 34.9 | 36.7 | 41.5 |
| Butyraldehyde | 100 | 100 | 48–48.5 |

*Butyraldehyde used herein was 90 weight percent n-butyraldehyde and 10 weight percent isobutyraldehyde.

In general, mineral oils contain paraffins, naphthenes and aromatic hydrocarbons. While aromatics per se do not generally interfere with the process of hydroformylation of alpha-olefins, they may cause problems with

TABLE V

Physical Properties of Decene Oligomer Solvents and Mineral Oils Used in Comparison

| Physical Constants | 6cSt* Decene Oligomer Solvent | 4cSt* Decene Oligomer Solvent | Mineral Oil Sunpar** 110 | Mineral Oil Sunpar** 150 | Mineral Oil Sunpar* 2280 |
|---|---|---|---|---|---|
| Viscosity (centistokes) | | | | | |
| 210° F. (99° C.) | 6.02 | 3.97 | 5.27 | 10.92 | 32.8 |
| 100° F. (38° C.) | 33.66 | 18.43 | 33.1 | 107.9 | 570.0 |
| Flash Point °F. | 456 | 430 | 385 | 490 | 580 |
| Specific Gravity 60/60 | 0.8270 | 0.8171 | 0.8510 | 0.870 | 0.892 |
| Composition Wt. % | | | | | |
| Carbon Atoms | | | | | |
| Paraffinics | 100 | 100 | 67 | 69 | 73 |
| Naphthenes | 0 | 0 | 29 | 27 | 23 |
| Aromatics | 0 | 0 | 4 | 4 | 4 |
| Carbon No. Distribution Wt. % | | | | | |
| $C_{30}$ | 31 | 80 | Unknown | Unknown | Unknown |
| $C_{40}$ | 46 | 20 | Unknown | Unknown | Unknown |
| $C_{50}$ | 23 | 0 | Unknown | Unknown | Unknown |

*Gulf Sunfluid ® White Oil - Gulf Oil Chemical Co.
**Sunpar Grades Paraffinic Rubber Process and Extender Oils Manufactured by Sun Oil Chemical Co.

Table VI describes propionaldehyde vapor pressure in various decene oligomer solvents and mineral oils of Table V.

TABLE VI

| Solvent | Propionaldehyde Concentration | | Propionaldehyde Vapor Pressure (psia) |
|---|---|---|---|
| | (Wt. %) | (Vol. %) | |
| 6cSt Decene Oligomer | 28–33 | 28.5–33.5 | 81.5 |
| " | 49.7 | 50.3 | 91.5 |
| " | 52.9 | 53.5 | 94.0 |
| 4cSt Decene Oligomer | 16.1 | 16.3 | 72.0 |
| " | 19.9 | 20.2 | 71.5 |
| " | 23.6 | 23.9 | 80.5 |
| " | 24.2 | 24.5 | 80.5 |
| Sunpar 110 Mineral Oil | 32.0 | 33.5 | 83.5 |
| " | 30.3 | 31.8 | 81.5 |
| " | 32.7 | 34.2 | 82.5 |
| " | 33.0 | 34.5 | 82.5 |
| Sunpar 150 Mineral Oil | 31.0 | 32.9 | 94.5 |
| " | 30.9 | 32.8 | 94.5 |
| Sunpar 2280 Mineral Oil | 35.0 | 37.4 | 95.0 |
| " | 38.2 | 40.7 | 95.0 |
| " | 43.2 | 43.8 | 95.0 |
| " | 41.1 | 43.7 | 95.0 |
| Pure Propionaldehyde | 100 | 100 | 96.5 |

Table VII describes butyraldehyde vapor pressure in 6cSt decene oligomer solvent and Sunpar 150 mineral oil of Table VI.

final product purity. In the use of alpha-olefin oligomers in the present invention, naphthenes and aromatics are not present and do not create a purity problem.

In many instances, mineral oils contain impurities such as sulfur and iron. Sulfur is a poison to the rhodium catalyst used in the process of this invention. Iron, as iron carbonyls, is an aldol catalyst for the aldehydes and would contribute to irreversible heavy ends production, resulting in efficiency loss. While these materials (iron and sulfur) could be removed or reduced to insignificant levels by special refining techniques, the necessity for such removal renders the process less economically attrative.

Saturated alpha-olefin oligomer solvents as used in the process of the present invention have the basic requirements for use as solvents in the hydroformylation process of alpha-olefins to their respective aldehydes. These solvent requirements include:
1. ease of separation of aldehyde product
2. ability to dissolve catalyst materials
3. low volatility to avoid solvent losses
4. low viscosity to reduce mass and heat transfer limitations
5. thermal and chemical stability
6. no contamination that could poison the catalyst or degrade product purity.

Alpha-olefin oligomer solvents as used in the process of this invention reduces the production of aldehyde by-product heavy ends since more aldehyde can be stripped from the reaction liquid than when the heavy ends are used as the main component of the solvent. With less aldehyde present in the reaction product solution, lower amounts of high heavy ends are produced and increased efficiencies of aldehyde production are obtained.

EXAMPLE 5

A comparison was made of the rousing factors resulting from the use of a decene oligomer (poly-alpha-olefin) solvent and a mineral oil solvent having similar viscosities each in combination with a catalyst solution obtained by stripping the reaction liquid resulting from the hydroformylation of propylene to butyraldehyde. The catalyst solution contained in addition to rhodium complex catalyst, a small amount (less than 4 weight percent) of butyraldehyde product, triphenylphosphine, triphenylphosphine oxide and in situ by-products resulting from the condensation of the product during the hydroformylation reaction.

When a gas is sparged through a quiescent liquid, the gas is held up in the liquid phase for a finite period of time. The total volume of gas liquid is thereby greater than the liquid volume alone, and has a reduced viscosity. This phenomenon of liquid volume expansion is called "rousing." The "rousing factor" is defined as the ratio of aerated volume to unaerated volume. The higher the rousing factor the lower the volume of liquid in the reactor which is available for reaction.

Rousing measurements were made using a two-inch diameter gas-sparged stainless steel reactor, seven feet high containing a sight glass along the length of the reactor to measure the volume of reactants. Reaction conditions at 300 psig. and 120° C. were maintained. Because of the butyraldehyde and light ends volatility, additional vent gas cooling and a condensed liquid recycle to the reactor were required to help maintain reactor composition and liquid level for reliable results. Nitrogen was sparged through a 1/16 inch orifice nozzle which was threaded into the lower head of the reactor column. Rousing factors on each fluid were obtained over a wide range of superficial gas velocities between 0.05 to 0.042 feet per second to insure adequate characterization of the fluids gassed behavior. These data points obtained were measured over a 30 to 40 minute period in obtaining constant rousing factors.

The properties of the decene oligomer solvent and mineral oil used in the comparison are shown in Table VIII.

TABLE VIII

| | Decene Oligomer* Solvent | Mineral Oil** |
|---|---|---|
| Viscosity (centistokes) | | |
| 210° F. (99° C.) | 6.02 | 7.10 |
| 100° F. (38° C.) | 33.66 | 56.4 |
| Flash Point °F. | 456 | 440 |
| Specific Gravity | 0.827 | 0.867 |
| Average Molecular Weight | 550 | 440 |

*Carbon number distribution $C_{30}$ = 31 weight percent, $C_{40}$ = 46 weight percent and $C_{50}$ = 23 weight percent. Sold under the trademark Synfluid ® base Fluids as Gulf 6cSt polyalpha-olefin by Gulf Oil Chemical Company.
**Sunpar 120 containing 4 weight percent aromatic carbon atoms, 28 weight percent naphthenic carbon atoms and 68 weight percent paraffinic carbon atoms. Sold by Sun Oil Chemical Co.

The rousing factors obtained using a combination of 50 weight percent decent oligomer (Table VIII) and 50 weight percent of the rhodium catalyst solution previously described at 300 psig. and 120° C. are shown in Table IX.

TABLE IX

| Superficial Gas Velocity ft/sec. | Rousing Factor |
|---|---|
| 0.034 | 1.06 |
| 0.057 | 1.25 |
| 0.117 | 2.15 |
| 0.184 | 3.39 |
| 0.278 | 3.32 |
| 0.331 | 3.13 |
| 0.448 | 2.87 |
| 0.478 | 2.87 |

Sufficient butyraldehyde was added to the combination of 50 weight percent decene oligomer and 50 weight percent of the rhodium catalyst solution previously described to provide a 30 weight percent butyraldehyde solution to determine the effect of a highly concentrated aldehyde product content on rousing. Conditions for rousing determination were 300 psig. and 120° C. Rousing factors obtained are shown in Table X.

TABLE X

| Superficial Gas Velocity ft/sec. | Rousing Factor |
|---|---|
| 0.029 | 1.037 |
| 0.050 | 1.44 |
| 0.106 | 2.80 |
| 0.150 | 3.46 |
| 0.220 | 3.33 |
| 0.313 | 3.14 |
| 0.390 | 2.88 |

The rousing factors obtained using a combination of a 50 weight percent mineral oil (Table VIII) and 50 weight percent of the rhodium catalyst solution previously described at 300 psig. and 120° C. are shown in Table XI.

TABLE XI

| Superficial Gas Velocity ft/sec. | Rousing Factor |
|---|---|
| 0.021 | 1.05 |
| 0.049 | 1.22 |
| 0.096 | 4.13 |
| 0.151 | 5.65 |
| 0.253 | 5.52 |
| 0.378 | 4.39 |

Sufficient butyraldehyde was added to the combination of 50 weight percent mineral oil (Table VIII) and 50 weight percent of the rhodium catalyst solution previously described to provide a 30 weight percent butyraldehyde solution to determine the effect of a highly concentrated product content on rousing. Conditions for rousing determination were 300 psig. and 120° C. Rousing factors obtained are shown in Table XII.

TABLE XII

| Superficial Gas Velocity ft/sec | Rousing Factor |
|---|---|
| 0.030 | 1.06 |
| 0.043 | 1.44 |
| 0.107 | 3.76 |
| 0.159 | 3.85 |
| 0.252 | 3.49 |
| 0.422 | 2.24 |

In the rousing factor comparisons of mineral oil solvents (Table XI) with equivalent decene oligomer solvent (Table IX), both containing low amounts of butyraldehyde present, the rousing factors of mineral oil product mixture are significantly higher than those of the decene oligomer product mixture at commercially acceptable superficial gas velocities of 0.10 to 0.40 ft/sec. As the rousing factor increases, the volume of liquid available for reaction in the reactor decreases. The data indicate that the use of a decene oligomer in a hydroformylation reaction, especially propylene to butyraldehyde, results in less rousing in the reactor and therefore a greater volume of liquid available for reaction in the reactor unit compared to the use of an equivalent mineral oil solvent. In a more concentrated butyraldehyde containing product as used in the results of Tables X and XII, higher rousing factors are obtained in the use of mineral oil solvent compared to the equivalent decene oligomer but differences in rousing factors are not as dramatic as in the reaction products containing lower amounts of butyraldehyde.

A different rhodium catalyst solution was used from that used in all of the samples of the prior tables describing rousing factors. The catalyst solution used also contained in addition to rhodium complex catalyst, a small amount (less than 4 weight percent) of butyraldehyde product, triphenylphosphine, triphenylphosphine oxide and in situ by products resulting from the condensation of the product during the hydroformylation reaction. Sufficient butyraldehyde was added to the combination of 50 weight percent mineral oil (Table VIII) and 50 weight percent of the rhodium catalyst solution previously described to provide a 30 weight percent butyraldehyde solution to determine the effect of a highly concentrated product content on rousing. Conditions for rousing were 300 psig. and 113° C. Rousing factors obtained are shown in Table XIII.

TABLE XIII

| Superficial Gas Velocity ft/sec. | Rousing Factor |
|---|---|
| 0.029 | 1.07 |
| 0.052 | 1.19 |
| 0.121 | 2.12 |
| 0.163 | 3.00 |
| 0.325 | 2.38 |
| 0.456 | 1.82 |

The rousing factors in Table XIII are slightly lower than those of Table XII. The catalyst sample was different and no other data are available for a comparison of rousing factors with an equivalent decene oligomer used in place of mineral oil.

What is claimed is:

1. In a process for hydroformylating an olefin of 2 to 20 carbon atoms having an ethylenic double bond in the alpha position by reacting said olefin at about 80° C. to about 150° C. and superatmospheric pressure with carbon monoxide and hydrogen in admixture with a liquid medium comprising a high boiling inert reaction solvent containing an effective amount of a hydroformylation catalyst comprising a Group VIII metal in complex combination with a ligand to form a liquid reaction product mixture comprising said ligand, an aldehyde derivative of said olefin and said high boiling inert reaction solvent, the improvement comprising employing, as said high boiling inert reaction solvent, a saturated alpha-olefin oligomer, free of naphthenic and aromatic hydrocarbons, containing molecules having from 30 to 50 carbon atoms, a flash point from about 400° F. to about 500° F., an average molecular weight from about 450 to about 700 and having a kinematic viscosity at 100° C. from about 3.0 to about 8.0 centistokes.

2. The process of claim 1 wherein the alpha-olefin oligomer has a flash point from about 425° F. to about 495° F., an average molecular weight from about 500 to about 570 and a kinematic viscosity at 100° C. from about 3.5 to about 6.5 centistokes.

3. The process of claim 2 wherein said olefin being hydroformylated is a monoalkene of 2 to 6 carbon atoms and the ligand is triphenylene phosphine.

4. The process of claim 1 wherein the alpha-olefin oligomer is produced by the polymerization of decene-1.

5. The process of claim 2 wherein the alpha-olefin oligomer is produced by the polymerization of decene-1.

6. In the process for hydroformylating propylene at about 100° to about 120° C. and superatmospheric pressure, which process comprises passing a gas with carbon monoxide, hydrogen and propylene through a liquid reaction medium contained in a hydroformylation reaction zone and containing a catalytically effective amount of a hydroformylation catalyst comprising a complex of rhodium with triphenylphosphine to form a reaction product comprising n-butyraldehyde the improvement comprising employing as the liquid reaction medium decene-1 oligomers containing molecules having from 30 to 50 carbon atoms, a flash point from about 425° F. to about 495° F., an average molecular weight from about 500 to about 570 and a kinematic viscosity at 100° C. from about 3.5 to about 6.5 centistokes.

7. In a process for hydroformylating ethylene at about 100° to about 120° C. and superatmospheric pressure, which process comprises passing a gas with carbon monoxide, hydrogen and ethylene through a liquid reaction medium contained in a hydroformylation reaction zone and containing a catalytically effective amount of a hydroformylation catalyst comprising a complex of rhodium with triphenylphosphine to form a reaction product comprising propionaldehyde, the improvement comprising employing as the liquid reaction medium a decene-1 oligomer composed of molecules having from 30 to 50 carbon atoms, a flash point from about 425° F. to about 495° F., an average molecular weight from about 500 to about 570 and a kinematic viscosity at 100° C. from about 3.5 to about 6.5 centistokes.

* * * * *